(12) United States Patent
Kureshy et al.

(10) Patent No.: US 7,429,360 B2
(45) Date of Patent: Sep. 30, 2008

(54) LEVEL-CONTROLLED PIPETTE FOR AUTOMATED ANALYTIC DEVICES

(75) Inventors: Fareed Kureshy, Del Mar, CA (US); Vijay K. Mahant, Murrieta, CA (US); Shailendra Singh, Carlsbad, CA (US)

(73) Assignee: Autogenomics, Inc., Carlsbad, CA (US)

( * ) Notice: Subject to any disclaimer, the term of this patent is extended or adjusted under 35 U.S.C. 154(b) by 409 days.

(21) Appl. No.: 10/509,986

(22) PCT Filed: May 28, 2003

(86) PCT No.: PCT/US03/17382

§ 371 (c)(1), (2), (4) Date: Nov. 2, 2004

(87) PCT Pub. No.: WO03/100442

PCT Pub. Date: Dec. 4, 2003

(65) Prior Publication Data

US 2005/0124059 A1  Jun. 9, 2005

Related U.S. Application Data

(60) Provisional application No. 60/383,896, filed on May 28, 2002.

(51) Int. Cl.
*B01L 3/02* (2006.01)
*G01F 25/00* (2006.01)

(52) U.S. Cl. ..................... 422/100; 73/1.74
(58) Field of Classification Search ............... 422/100; 73/1.74

See application file for complete search history.

(56) References Cited

U.S. PATENT DOCUMENTS 5,141,871 A * 8/1992 Kureshy et al. ............ 436/47
6,948,843 B2 * 9/2005 Laugharn et al. ........... 366/127

OTHER PUBLICATIONS

Definition of "coupled"; Merriam-Webster Online Dictionary; downloaded from http://www.m-w.com/cgi-bin/dictionary?book=Dictionary&va=coupled; downloaded Nov. 15, 2007.*

* cited by examiner

*Primary Examiner*—Jon D. Epperson
*Assistant Examiner*—Sue Liu
(74) *Attorney, Agent, or Firm*—Fish & Richardson, PC

(57) ABSTRACT

An automatic pipette in an analytic device uses disposable pipette tips, and in which proper coupling of the pipette tip to the pipette, accurate volume of the aspirated fluid, and distance of the pipette tip to a biochip are determined using a plurality of sensors that are coupled to the automatic pipette.

9 Claims, 3 Drawing Sheets

US 7,429,360 B2

LEVEL-CONTROLLED PIPETTE FOR AUTOMATED ANALYTIC DEVICES

This application claims the benefit of U.S. provisional patent application with the Ser. No. 60/383,896, filed May 28, 2002, and international patent application with the serial number PCT/US02/17006, filed May 29, 2002, both of which are incorporated herein by reference.

FIELD OF THE INVENTION

The field of the invention is pipettes, and particularly pipettes in automated analytic devices.

BACKGROUND OF THE INVENTION

Numerous automatic pipettes are known in the art and may be grouped into various categories. For example, some automatic pipettes employ positive displacement of a plunger that moves within a preformed tip to aspirate a desired volume, while other pipettes employ a pump (air interface pipette) that provides a reduced pressure that is sufficient for aspiration of the desired volume.

Positive displacement pipettes generally provide numerous advantages. For example, cross contamination between different samples aspirated by the same pipette (e.g., via aerosol) is virtually eliminated. Moreover, positive displacement pipettes often provide significantly higher accuracy and precision that is typically not achieved with air-interface pipettes, especially where high-vapor pressure liquids, detergent containing fluids, and/or volatile solvents are aspirated. However, such pipettes generally require close-tolerance manufactured pipette tips, which are relatively expensive. Moreover, disposable close-tolerance manufactured pipette tips for positive displacement pipettes are typically not available for use in an robotic pipettors. Alternatively, non-disposable pipette tips (e.g., Teflon coated tips) for positive displacement pipettes may be used in robotic pipettors. However, cross contamination frequently occurs unless specific additional cleaning steps are implemented into a robotic pipetting operation.

Air interface pipettes advantageously combine relatively inexpensive operation with satisfactory accuracy and precision for many applications. For example, where in a robotic air interface pipettor non-disposable tips are employed, a single vacuum pump may control multiple pipette channels, which decreases operating cost due to reduced maintenance of moving parts. However, cross contamination may arise, especially where no additional cleaning steps are implemented. To circumvent some of the problems with cross contamination, disposable pipette tips may be employed. However, and especially in robotic pipettors with multi-channel operation, disposal of used pipette tips may become problematic where the pipettor is enclosed within an analytic device.

Regardless of the type of pipette (i.e., air interface or positive displacement), further difficulties arise with the use of disposable pipette tips. Most significantly, where disposable pipette tips are engaged with (i.e., picked up by) a pipettor via a robotic mechanism, even relatively slight misalignment between the pipette tip and the pipettor will often result in a gap through which air is aspirated during a pipetting operation. Consequently, the volume of fluid in the pipette tip is lower than the volume that was intended to be aspirated. Moreover, since disposable pipette tips often have a relatively large manufacturing tolerance, the exact position of the tip of a pipette tip is difficult to predict. This becomes particularly problematic where surface tension of microliter and submicroliter volumes requires close approximation of the tip to the surface where the volume is to be deposited.

Thus, although various systems for pipettes are known in the art, numerous problems still remain. Therefore, there is still a need for an improved methods and systems for automated pipettes, and especially those that employ disposable pipettes.

SUMMARY OF THE INVENTION

The present invention is directed to an automatic level-controlled pipette in which one or more sensors detect the presence and fill level of a pipette tip and the position of the pipette tip relative to a surface onto which the fluid is to be deposited. Particularly contemplated automatic level-controlled pipette are part of an analytic device.

In one aspect of the inventive subject matter, an analytic device with an automatic pipette will include a pipette tip receiving element that is coupled to a mechanism that translates the pipette tip receiving element along at least two of an x-coordinate, a y-coordinate, and a z-coordinate, wherein the pipette tip receiving element is further operationally coupled to a sensor that detects presence of a disposable pipette tip that is removably coupled to the pipette tip receiving element. A first energy source and a first energy detector are coupled to the pipette tip receiving element wherein the first energy source provides a first energy to a volume that is enclosed by the pipette tip, and wherein first energy detector receives at least a portion of the first energy from the volume. A second energy source and a second energy detector are coupled to the pipette tip receiving element wherein the second energy source provides a second energy to a surface of a biochip when the pipette tip approaches the surface of the biochip, and a processor is electronically coupled to the first and second energy detectors, wherein the processor controls accurate aspiration of a predetermined volume using a signal from the first detector, and wherein the processor controls movement of the pipette tip along a z-coordinate using a signal from the second detector.

The first energy source in especially preferred analytic devices comprises a laser, wherein the first energy is provided to the volume via a light guide. In such devices, accurate aspiration may then be calculated from reflected laser light that is detected by the first energy detector. The second energy source may advantageously comprise a sonic transducer (e.g., an ultrasound transducer), while the sensor is preferably an optoelectronic sensor. Disposable pipette tips will generally have various volumes, however, volumes of 200 microliter and less are especially preferred. With respect to the mechanism it is generally preferred that the mechanism comprises a robotic arm that translates the pipette tip receiving element along the x-, y-, and z-coordinate.

Contemplated analytic devices may further include a data transfer interface, that provides data to the operator or a person other than the operator (e.g., in a remote place relative to the analytic device). Alternatively, or additionally, contemplated analytic devices may also include a sample station with a multi-well plate and a multi-reagent pack, wherein the pipette tip removes a fluid from the multi-well plate and/or the multi-reagent pack and dispenses the fluid onto the surface of the biochip.

Thus, viewed from another perspective, it is contemplated that an automatic pipette in an analytic device includes a disposable pipette tip and a first and a second sensor, wherein the first sensor detects a volume of a liquid within the pipette tip and wherein the second sensor detects a vertical distance between the pipette tip and a biochip that is disposed in the analytic device.

The first sensor in particularly preferred automatic pipettes will include a laser that delivers a laser beam into the pipette tip, wherein the volume of the liquid is determined by destructive interference, constructive interference, phase modulation, and/or triangulation. Preferred second sensors comprise an ultrasound transducer that delivers a sound beam to the surface of the biochip, wherein the vertical distance is determined using a time-of-flight algorithm. Additionally, contemplated automatic pipettes may further include a third sensor that detects coupling of the disposable pipette tip to the automatic pipette.

Various objects, features, aspects and advantages of the present invention will become more apparent from the following detailed description of preferred embodiments of the invention, along with the accompanying drawing.

DETAILED DESCRIPTION

Figure 1:
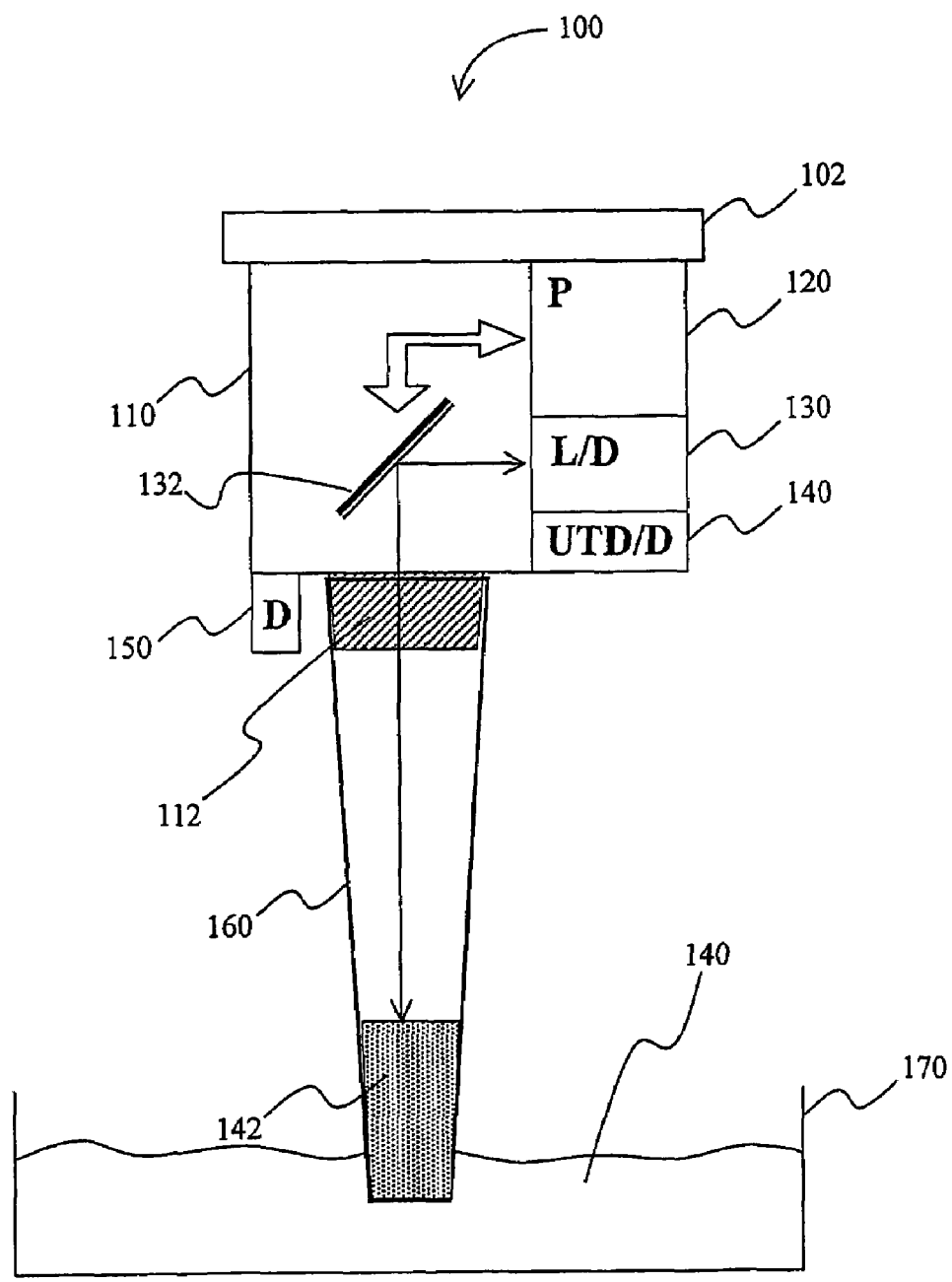
FIG. 1 is a schematic view of an exemplary automatic level-controlled pipette aspirating a fluid from a fluid source.

As used herein, the term "analytic device" refers to a device in which a sample is processed in one or more steps to detect the presence and/or quantity of one or more particular analytes, or in which an analyte is processed in one or more steps to determine a physical and/or chemical property of the analyte. Particularly preferred analytic devices are described in our copending and commonly owned international patent application with the serial number PCT/US02/17006 (supra). Consequently, particularly preferred analytic devices will include an optical detector, one or more reagent reservoirs and/or sample reservoirs, and an automatic pipette.

As also used herein, the term "automatic pipette" generally refers to a pipette in which aspiration and dispensation of a fluid is performed using an electronically operated device (e.g., vacuum pump or plunger-type pump driven by a stepper motor or direct drive motor), and in which the pipette is moved along at least one coordinate without manual user intervention. The term "moved . . . without manual user intervention" as used herein means the pipette is moved without the user physically touching (e.g., manually gripping or lifting) the pipette, however, does not exclude manual programming (e.g., typing on a keyboard or touch screen) of the analytic device to effect automatic movement of the pipette. Particularly suitable automatic pipettes include single-channel pipettes, however, multi-channel pipettes are (while not preferred) not specifically excluded.

As further used herein, the term "disposable pipette tip" refers to a tip which is under normal use conditions employed for single use (i.e., aspiration of a desired volume into the tip, followed by dispensation of at least part of the aspirated volume, followed by discarding of the tip). Disposable pipette tips are typically manufactured from a polymer (e.g., polyethylene) and are commercially available from numerous sources.

As still further used herein the term "the processor controls accurate aspiration of a predetermined volume" means that a processor (e.g., microprocessor of a computer that is electronically coupled to the automatic pipette, or a dedicated microprocessor) determines the actual volume of fluid aspirated into the pipette tip using a signal provided by a detector, wherein aspiration is terminated once the determined volume is substantially identical (i.e., 5%, more typically 2.5%, and most typically less than 1.5% coefficient of variation) with the predetermined volume.

As also used herein, the term "biochip" refers to an array of probes which are coupled to a substrate in a plurality of predetermined positions. Suitable biochips may be at least partially disposed within a housing, and particularly preferred biochips are described in our commonly-owned and copending U.S. patent application Ser. No. 10/346,879, filed Jan. 17, 2003, and the PCT applications with the serial numbers PCT/US02/03917, filed Jan. 24, 2002, and PCT/US01/47991, filed Dec. 11, 2001, all of which are incorporated by reference herein.

The inventors discovered that an automatic pipette using disposable pipette tips can be operated without manual user intervention at relatively high accuracy/precision when a plurality of sensors control various functions of the automated pipette. In one preferred example, as shown in FIG. 1, an exemplary pipettor 100 of an analytic device includes a robotic arm 102 to which a pipette tip receiving element 110 is coupled. Pump 120 is pneumatically coupled to the pipette tip receiving element 110, and laser/detector element 130 is optically coupled to the pipette receiving element 110. Ultrasound transducer/detector element 140 and optoelectronic detector 150 are further coupled to the pipette receiving element 110. A disposable pipette tip 160 with aspirated fluid 142 is removably coupled to the fitting 112, while the tip of the pipette tip 160 is immersed in fluid 140, which is retained by container 170.

To aspirate fluid, a controller circuit positions robotic arm 102 over a fluid-filled container, and moves the tip of disposable pipette tip 160 below the surface of the fluid. Once the tip of the disposable pipette tip is in proper position (e.g., which may be a predetermined position), pump 120 starts removing air from the pipette receiving element 110, thereby creating an under pressure, which forces fluid 140 into the tip. While the pump is in operation, the laser from the laser/detector element 130 provide a light beam (thin arrow) via mirror 132 into the pipette tip, and the laser light is reflected by the fluid as the fluid is aspirated into the pipette tip 160. The so reflected light travels via mirror 162 to the detector of the laser/detector element 130, and the distance between the first position of reflection (i.e., entry of the fluid into the tip) and subsequent positions of reflection is continually measured using destructive and/or constructive interference. Based on the height difference between the first position and the subsequent positions, the volume of aspirated liquid is calculated by a processor, which stops the pump 120 when the measured volume is substantially the same (i.e., 5%, more typically 2.5%, and most typically less than 1.5% coefficient of variation) as a predetermined volume.

Figure 2:
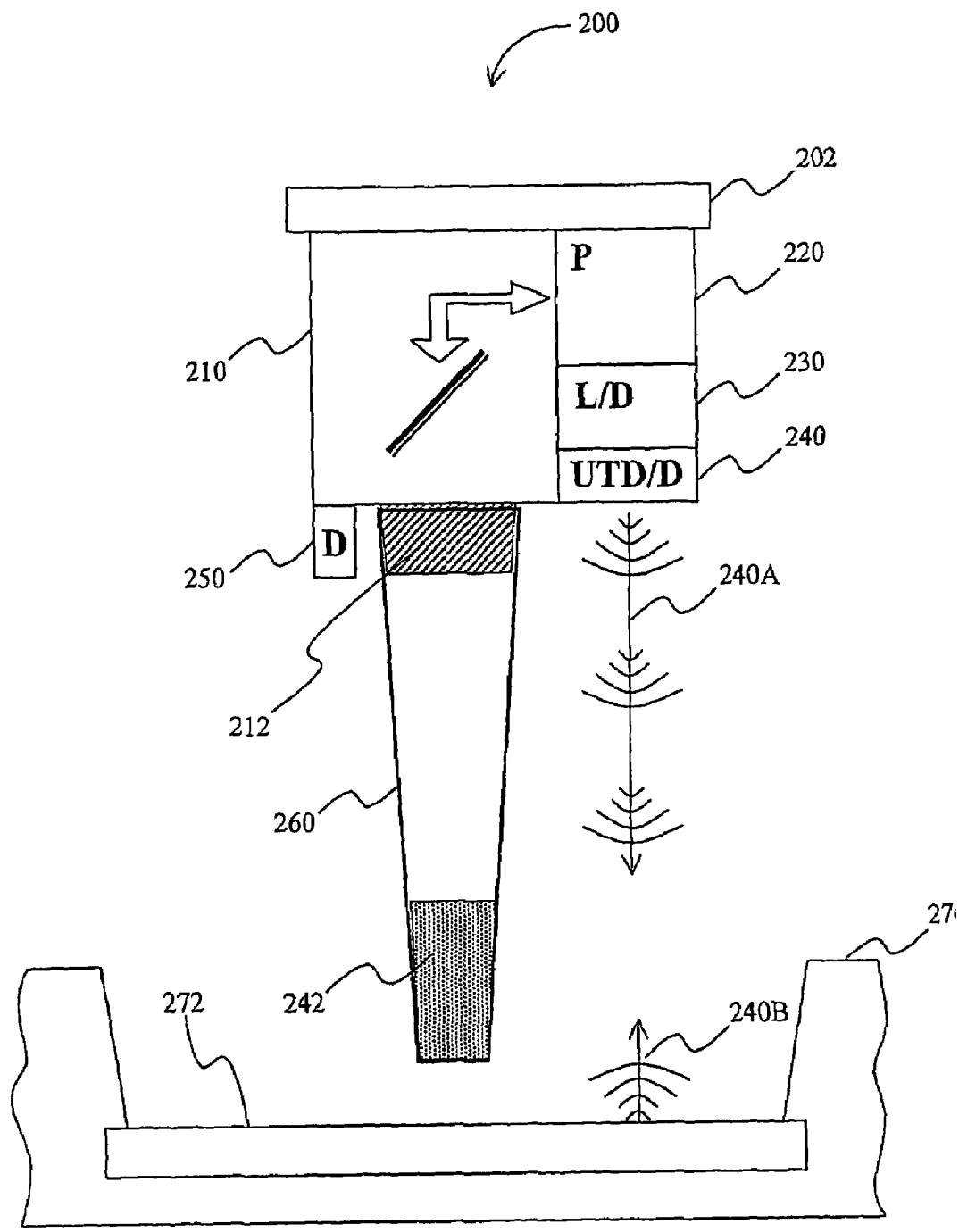
FIG. 2 is a schematic view of an exemplary automatic level-controlled pipette approaching the surface of a biochip.

FIG. 2 schematically depicts exemplary pipettor 200 (which is the pipettor of FIG. 1 in which like numerals refer to like components), now located over the biochip 272, which is coupled to the housing 270. The pipette tip 260, while remaining engaged with the fitting 212 holds the aspirated fluid 242. As in FIG. 1, the pipettor 200 includes pipette tip receiving element 210, to which are coupled the optoelectronic detector 250, the pump 220, the laser/detector element 230, and the ultrasound transducer 240/detector 240. As the robotic arm 202 with the pipette tip receiving element 210 approaches the biochip 272 along the z-coordinate (i.e., in a vertical movement), the ultrasound transducer emits ultrasound energy 240A directed towards the biochip (and/or the housing) 272. From the reflected ultrasound energy 240B, the vertical distance between the biochip and the pipette tip receiving element 210 (and/or tip of the pipette tip) is calculated by a processor using a time-of-flight algorithm. Once the tip of the pipette tip is in a desired position, the fluid 242 is dispensed onto the surface of the biochip 272.

Figure 3:
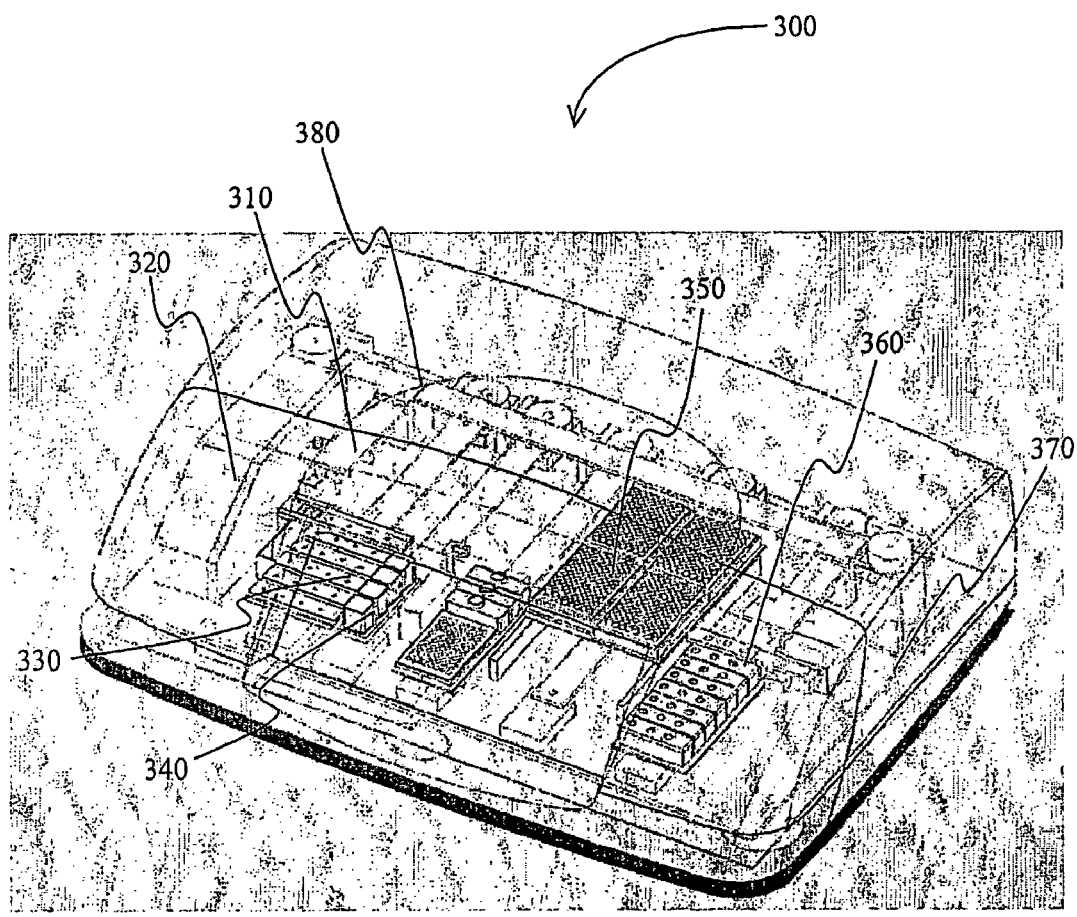
FIG. 3 is a schematic view of an exemplary analytic device that includes an automatic level-controlled pipette.

FIG. 3 depicts an exemplary analytic device 300 in which a pipettor 310 is integrated. Here, a detector 320 detects an analyte signal from a biochip that is moved from a multi-biochip magazine 340 via a sample processing platform 330 to the detector 320. A fluid sample is transferred from a multi-well plate of sample station 350 with the pipettor 310, while reagents are transferred from the multi-reagent packs 360 to the biochip on the sample processing platform 330 using pipettor 310. In such exemplary devices, the robotic arm of the pipettor further includes a manipulator (which may be separately movable—e.g., linear or rotational) to push the biochip from one location in the analytic device to the next. Operation of the pipettor and optionally other components is controlled by processor 380. A data transfer interface 370 provides connectivity to a computer outside of the analytic device (not shown). Particularly suitable analytic devices are described in copending international patent application with the serial number PCT/US02/17006, filed May 29, 2002 (supra).

With respect to the pipette tip receiving element, it is generally preferred that the pipette tip receiving element is pneumatically coupled to a pump and includes a fitting that releasable engages with a disposable pipette tip (infra). Therefore, the shape and size of suitable pipette tip receiving elements may vary substantially. For example, where the pump has an elongate portion, the pipette tip receiving element may be integral with and formed by the pump. On the other hand, and especially where the laser/detector element is coupled to the pipette tip receiving element such that the laser beam requires at least one change in direction to be guided into the tip, suitable pipette tip receiving elements may be box-shaped, cylinder shaped, or irregularly shaped. Thus, and viewed from another perspective, contemplated pipette tip receiving elements will generally include a hollow portion that pneumatically couples the pump with the pipette tip, and it is further preferred that the laser beam passes through at least part of the hollow portion, wherein the laser beam may be directed through the hollow or guided through the hollow portion (e.g., via a fiber optic cable). In further contemplated aspects, the pipette tip receiving element may also be completely omitted, or be integrated into the pump.

There are numerous suitable fittings contemplated for use in conjunction with the teachings presented herein, and it should be recognized that all known pipette tip fittings are deemed suitable so long as such fittings are configured to receive and at least temporarily retain a disposable pipette tip. For example, the fitting may be an integral structure of the pipette tip receiving element or the pump wherein the pipette tip engages with a frustroconical structure (e.g., similar as to the tip of a manual pipette using disposable pipette tips). In another example, the fitting may also be a separate be frustroconical pipe that is pneumatically coupled to the pipette tip receiving element. With respect to the material for the fitting (as well as for the pipette tip receiving element), it should be appreciated that numerous materials are deemed suitable. For example, preferred materials include metals, metal alloys, synthetic polymers, and all reasonable combinations thereof.

It should further be appreciated that all commercially available disposable pipette tips are suitable for use in conjunction with the teachings presented herein. However, particularly preferred pipette tips include those with a volume of equal or less than 1000 microliter, and more typically 200 microliter (The term "volume of equal or less than . . . microliter" refers to the fluid volume for which such tips are typically designed. Therefore, while a tip may be designed for equal or less than 200 microliter, the actual inner volume defined by the walls of the tip may be 350 microliter, or even more). Furthermore, where appropriate, custom-made pipette tips are also deemed suitable (e.g., to include a specific volume, or to achieve a particular optical or other physical property).

Thus, the particular nature of the sensor that detects the presence of the pipette tip at the pipette tip receiving element may vary considerably, and it should be recognized that numerous sensors other than an optoelectronic sensor (i.e., a photodiode that detects light reflected from the tip, wherein the light is provided by an LED) are also suitable. For example, where illumination is less preferred, suitable sensors may include mechanical sensors (e.g., comprising a movable element that opens or closes an electrical circuit in the presence of absence of the pipette tip), electrical sensors (e.g., where the pipette tip insulatingly interrupts an electrical circuit), and/or magnetic sensors (e.g., where at least part of the pipette tip comprises a magnetic portion).

Similarly, contemplated pipettors may be coupled to various mechanisms that translate the pipette tip receiving element along at least one, and more preferably at least two coordinates. However, it is generally preferred that the pipette tip receiving element is coupled to a robotic arm that is movable coupled to a rail or other guiding structure that provides movement along the x-coordinate, while the pipette tip receiving element is movable coupled to a robotic arm along the y- and z-coordinate. Alternatively, and especially where movement of the robotic arm along the x-coordinate is less preferred, a robotic arm with a rotating base may be employed. In still further contemplated aspects, the robotic arm may also provide movement of the pipette tip receiving element along only two coordinates, while movement of the receiving element along a third coordinate relative to the biochip, sample processing platform or other structure may be provided by moving the biochip, sample processing platform or other structure along the third coordinate. Still further contemplated robotic arms may optionally further comprise a mechanism that removes the disposable pipette tip.

Suitable pumps for contemplated pipettors may vary considerably, and it is generally contemplated that all known pumps for automatic pipettes may be used, as long as the pump will provide aspiration and dispensation of a fluid into and from a disposable pipette tip. Contemplated pumps may therefore include stepper motors, liner motors, direct drive motors, piezo motors, etc. that actuate a membrane vacuum pump or a plunger-type vacuum pump. Thus, the pump may be directly coupled to the pipette tip receiving element or indirectly via a pneumatic conduit. In still further contemplated aspects, the pump may also form at least part of the pipette tip receiving element and/or fitting. With respect to the volume of fluid that can be aspirated for a single aspiration with suitable pumps (e.g., plunger-type pump), it should be recognized that preferred volumes will generally be less than 10 ml, more typically less than 5 ml, and most typically less than 2 ml. On the other hand, where membrane or other pumps are employed, limiting volumes are typically not encountered. While not particularly preferred, it should also be recognized that the pump may also be replaced by a vacuum line and/or pressurized line. In such configurations, control over aspiration and/or dispensing is preferably performed using solenoids that open/close the vacuum and/or pressurized line.

In further particularly preferred aspects, the pump is electronically controlled by a processor, wherein specific control modes will vary with a particular application. However, it is preferred that the control modes will generally include operator-directed control (e.g., operator instructing processor to aspirate or dispense a specific volume), and software-directed control (e.g., software maintains aspiration until a the volume of fluid in the pipette tip is identical with a predetermined volume).

With respect to the laser/detector element, it is generally contemplated that all laser/detector elements are suitable so long as such elements can be used to determine a distance between the detector and the surface of a fluid that is aspirated into the pipette tip. Thus, suitable elements may operate using various configurations and algorithms, and especially preferred elements will be configured to operate using time-of-flight detection, interference and/or phase detection, strength of reflection, and/or triangulation detection. Thus, suitable laser/detector elements may include additional components. For example, where the distance is calculated using the light phase and a destructive/constructive interference algorithm, a modulator may be included. On the other hand, where the distance is calculated via time-of-flight, a timer may be included. In still further examples, where the distance is calculated via triangulation, supplemental optics (e.g., mirror, prism, etc) may be included. There are numerous laser distance measures commercially available and known in the art, and all of such measures are considered suitable for use herein.

Depending on the particular positioning of the laser/detector element relative to the pipette tip, it should be recognized that light guides may be added to direct and/or collect light required for the determination of the distance. Suitable light guides include fiber optics, mirrors, and/or channels through which at least a portion of the emitted and/or reflected light passes. Therefore, in at least some of the contemplated devices, the laser/detector elements may be optically coupled to the pipette tip receiving element via light guide. Alternatively, and especially where the laser beam from the laser/detector element is coaxial with the central axis of the pipette tip, a light guide may be entirely omitted, or may be formed by a passageway between the laser/detector element and the pipette tip.

In further alternative aspects of the inventive subject matter, the distance may also be calculated using energy sources other than a laser and energy detectors other than a photodiode. For example, alternative optical detection may include distance determination using polarized light. Therefore, suitable first energy sources may include polychromatic light sources (e.g., incandescent, fluorescent). Moreover, it should also be appreciated that alternative first energy sources may also be non-optical energy sources, and especially preferred alternative sources will include an ultrasound transducer. There are numerous ultrasound transducers for measuring a distance known in the art (infra), and all of such transducers are considered suitable for use herein so long as the ultrasound energy is directed into and received from the pipette tip. Similarly, non-ultrasound acoustic transducers (or separate transmitter and receiver) are also contemplated suitable for use herein. While it is generally contemplated that an ultrasound transducer operates in a pulse-echo mode, it is also contemplated (and particularly where separate transmitters and receivers are used) that pitch-catch arrangements may also be employed.

Moreover, it should be recognized that while it is preferred that a first energy is employed for detection of the volume of aspirated fluid in the disposable pipette tip, aspiration of a predetermined volume may also be achieved by without a first energy source and detector. For example, suitable volumes may be aspirated by electronic control of pump time and/or pump speed. Alternatively, the volume of the aspirated fluid may indirectly be determined by volume control of the container from which the fluid is aspirated. In yet another preferred aspect, the first detector may also be employed to measure the amount of fluorescence of a fluid that is aspirated. The so measured fluorescence may then be used to determine the volume within the tip.

It is generally preferred that the second energy source for determination of the distance between the biochip and the pipette tip and/or pipette tip receiving element comprises an acoustic energy source, and all suitable acoustic energy sources are considered suitable for use herein. For example, suitable acoustic energy sources include an ultrasound transducer/receiver, and a non-ultrasound acoustic transducer/receiver. The term "transducer" as used herein refers to a device that converts electric energy into acoustic energy, and may further also convert acoustic energy to electric energy. Therefore, a transducer may be employed as transmitter alone, or may be operated as transmitter and receiver. Such configurations are particularly advantageous where the biochip comprises a plurality of analytes bound a plurality of probes, wherein at least some of the analytes further include a photolabile compound.

There are numerous acoustic distance measuring devices known in the art, and all of such devices are contemplated suitable for use herein. However, it is especially preferred that the acoustic transducer/detector operates under conditions that will provide a signal resolution of less than 5 mm, more preferably less than 2 mm, and most preferably less than 1 mm. Therefore, it is generally preferred that the transducer is an ultrasound transducer or a sonic transducer operating at a frequency between of about 7-15 kHz. Where the transducer is operated as transmitter and receiver, a pulse-echo mode is generally preferred where the time-of-flight is employed to determine the distance between the transducer and the biochip (or other surface, including fluid surface of a reagent in a reagent container or sample fluid surface in a multi-well plate). On the other hand, it is also contemplated that the transmitter and detector may be spatially separated. Therefore, the acoustic distance measuring device may also operate in a pitch-catch arrangement and the distance between the transmitter and the biochip or other surface may be determined using time-of-flight or triangulation.

Of course, it should be recognized that the distance between the transmitter and the biochip or other surface can then be employed to calculate the distance between the tip of the pipette tip and the biochip or other surface provided the length of the disposable pipette tip and/or the spatial relationship between the transducer and the tip of the pipette tip is known. Such distance determination is especially preferred where the correct positioning of a pipette tip relative to a fluid surface or solid surface is desired in an automated system where the pipettor approaches such surfaces. Feedback for correct position will then be provided by the acoustic detector as the pipette tip approaches (along the z-coordinate) a surface. Thus, the second energy may advantageously be employed to ensure that the tip of the disposable pipette tip is in contact with the surface or immersed in the fluid that is to be aspirated. Furthermore, such contemplated configurations allow deposition of a fluid to the surface of a biochip such that the tip of the disposable pipette tip will not contact the surface of the biochip, which is particularly important where the biochip is moved by an actuator within an automated analytic device. Moreover, use of an acoustic energy will further prevent inadvertent photodeleterious effects (e.g. photobleaching of a fluorescence label) that would otherwise be likely to occur where distance determination is performed with an optical system that requires illumination of the biochip. However, it should be recognized that optical detection using a light source and a detector as described above for the first energy source are not excluded for use in conjunction of the second energy source.

With respect to the processor, it is generally contemplated that the processor may be integrated into the analytic device and controls further functionalities of the analytic device (e.g., detector, movement of a robotic arm, temperature control of a the sample processing platform, pipette motor, etc.). Alternatively, the processor may be also be a dedicated processor that electronically communicates with the first or second energy source and at least one other component of the analyzer. However, it is preferred that the processor is electronically coupled to the pipette motor, the robotic arm, and first and second energy detectors, wherein the processor controls accurate aspiration of a predetermined volume using the signal from the first detector, and wherein the processor controls movement of the pipette tip along a z-coordinate using the signal from the second detector.

Contemplated analytic devices may advantageously include a data transfer interface that is electronically coupled to the automatic pipettor or a computer that controls operation of the analytic device/pipettor. Such data transfer interfaces (e.g., telephonic, DSL, or cable modem) may transfer operational parameters from the pipettor to another computer to provide status information or troubleshooting guidance for the analytic device, or to provide access to remote operation. For example, the pipettor may include various sensors that provide feedback on operating condition, presence of disposable tip, environmental parameters, etc. to generate a status code (e.g., aspiration in progress, "no pipette tip" alarm, etc.) that may then be transferred to the operator of the analytic device as well as to a person other than the operator, which may be in a remote location relative to the analytic device (e.g., at a different ZIP code, different city, county, or even state).

Therefore, in one especially preferred aspect, the inventors contemplate an analytic device with an automated pipette in which a pipette tip receiving element is coupled to a mechanism that translates the pipette tip receiving element along at least two of an x-coordinate, a y-coordinate, and a z-coordinate. The pipette tip receiving element is further operationally coupled to a sensor that detects presence of a disposable pipette tip that is removably coupled to the pipette tip receiving element. A first energy source and a first energy detector are coupled to the pipette tip receiving element wherein the first energy source provides a first energy to a volume that is enclosed by the pipette tip, and wherein first energy detector receives at least a portion of the first energy from the volume. A second energy source and a second energy detector are coupled to the pipette tip receiving element wherein the second energy source provides a second energy to a surface of a biochip when the pipette tip approaches the surface of the biochip, and a processor is electronically coupled to the first and second energy detectors, wherein the processor controls accurate aspiration of a predetermined volume using a signal from the first detector, and wherein the processor controls movement of the pipette tip along a z-coordinate using a signal from the second detector. Such devices may further a include a sample station with a multi-well plate and a multi-reagent pack, wherein the pipette tip removes a fluid from at least one of the multi-well plate and the multi-reagent pack and dispenses the fluid onto the surface of the biochip. Viewed from another perspective, the inventors contemplate an automatic pipette in an analytic device, comprising a disposable pipette tip and a first and a second sensor, wherein the first sensor detects a volume of a liquid within the pipette tip and wherein the second sensor detects a vertical distance between the pipette tip and a biochip that is disposed in the analytic device.

Further especially contemplated analytic devices may also include a multi-reagent pack, an optical detector, and a integrated sample processing platform to form an integrated analytic device. Particularly preferred multi-reagent packs contemplated in conjunction with the teachings presented herein include those described in our co-pending international patent application with the title "Multi-Reagent Pack", filed May 28, 2003, which is incorporated by reference herein. Particularly preferred sample processing platforms contemplated in conjunction with the teachings presented herein include those described in our co-pending international patent application with the title "Integrated Sample Processing Platform", filed May 28, 2003, which is incorporated by reference herein. Particularly preferred optical detectors contemplated in conjunction with the teachings presented herein include those described in our co-pending international patent application with the title "Microarray Detector and Methods", filed May 28, 2003, which is incorporated by reference herein.

Thus, specific embodiments and applications of automatic level-controlled pipettes have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An analytic device with an automatic pipette, comprising:
    a robotic arm comprising (1) a pipette tip receiving element and (2) a manipulator, wherein the robotic arm is configured to allow translation of the pipette tip receiving element along at least two of an x-coordinate, a y-coordinate, and a z-coordinate, wherein the manipulator is configured to allow pushing of a biochip from one location in the analytic device to another location, and wherein the manipulator is further configured to allow movement of the manipulator in a linear and in a rotational motion;
    wherein the pipette tip receiving element further comprises a sensor, wherein the sensor is configured to allow detection of presence of a disposable polymer pipette tip, and wherein the receiving element is further configured to allow removable coupling of the disposable polymer pipette tip to the pipette tip receiving element;
    a first energy source and a first energy detector operably coupled to the pipette tip receiving element, wherein the first energy source is configured to allow providing of a first energy to a volume of a liquid that is aspirated into the pipette tip without passing across a wall of the tip, and wherein the first energy detector is configured to allow receiving at least a portion of the first energy from the volume without the portion of the first energy passing across the wall of the tip;

a second energy source and a second energy detector structurally coupled to the pipette tip receiving element, wherein the second energy source is configured to allow providing of a second energy to a surface of a biochip when the pipette tip approaches the surface of the biochip, and wherein the second energy detector is configured to allow receiving at least part of the second energy from the surface; and a processor electronically coupled to the first and second energy detectors, wherein the processor is configured to allow calculation of an accurate aspiration volume of a predetermined volume using a signal from the first detector, and wherein the processor is further configured to allow control of movement of the pipette tip along a z-coordinate using a signal from the second detector.

2. The analytic device of claim 1 wherein the first energy source comprises a laser, and wherein the first energy is provided to the volume via a light guide.

3. The analytic device of claim 2 wherein the processor is further configured to allow calculation of accurate aspiration from a reflected light signal that is detected by the first energy detector.

4. The analytic device of claim 2 wherein the second energy source comprises an ultrasound transducer.

5. The analytic device of claim 1 wherein the sensor comprises an optoelectronic sensor.

6. The analytic device of claim 1 wherein the disposable pipette tip has a volume of equal or less than 200 microliter.

7. The analytic device of claim 1 further comprising a data transfer interface that is configured to allow export of data from the device.

8. The analytic device of claim 1 wherein the data transfer interface is configured to allow providing of data to a person other than the operator, wherein the person is in a remote location relative to the analytic device.

9. The analytic device of claim 1 further comprising a sample station with a multiwell plate and a multi-reagent pack, wherein the robotic arm is further configured to allow removal of a fluid from the multi-well plate and the multi-reagent pack and dispensation of the fluid onto the surface of the biochip using the pipette tip.

* * * * *